United States Patent [19]

Phillips

[11] Patent Number: 4,595,011
[45] Date of Patent: Jun. 17, 1986

[54] TRANSDERMAL DOSIMETER AND METHOD OF USE

[76] Inventor: Michael Phillips, 1740 Hinman Ave., Apt. 3B, Evanston, Ill. 60201

[21] Appl. No.: 632,127

[22] Filed: Jul. 18, 1984

[51] Int. Cl.$^4$ .............................................. A61B 5/00
[52] U.S. Cl. .................................. 128/636; 128/760; 128/771; 128/638; 204/403
[58] Field of Search ............. 128/760, 771, 762, 632, 128/635, 636, 638, 640; 204/403; 435/817; 422/58; 604/312

[56] References Cited

U.S. PATENT DOCUMENTS

| | | | |
|---|---|---|---|
| 3,216,411 | 11/1965 | Watanuki et al. ................. | 128/638 |
| 4,220,158 | 9/1980 | Delpy et al. ...................... | 128/632 |
| 4,224,125 | 9/1980 | Nakamura et al. ............... | 204/403 |
| 4,329,999 | 5/1982 | Phillips ............................. | 156/247 |
| 4,444,193 | 4/1984 | Fogt et al. ........................ | 128/636 |
| 4,454,007 | 6/1984 | Pace .................................. | 204/403 |

*Primary Examiner*—Edward M. Coven
*Attorney, Agent, or Firm*—Kane, Dalsimer, Kane, Sullivan and Kurucz

[57] ABSTRACT

A transdermal dosimeter, a device used to monitor exposure to chemical agents is disclosed. The device is attached to the skin surface and functions by causing the uptake of compounds that are excreted through the skin.

31 Claims, 6 Drawing Figures

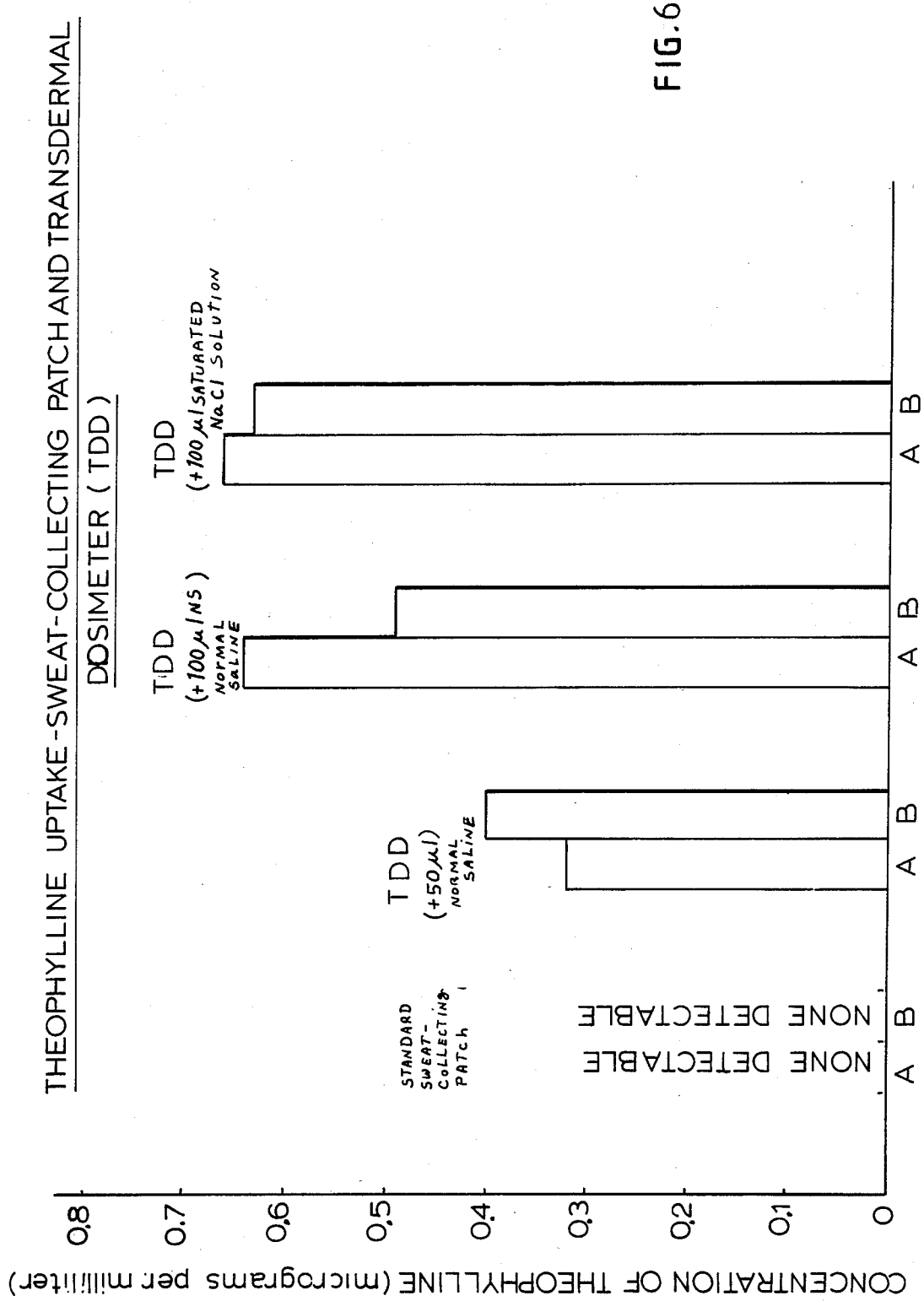

TRANSDERMAL DOSIMETER AND METHOD OF USE

FIELD OF THE INVENTION

The invention relates to a transdermal dosimeter, a device used to monitor human and animal exposure to chemical agents.

BRIEF DESCRIPTION OF THE PRIOR ART

The present invention, a transdermal dosimeter, is a device used to monitor human exposure to chemical agents; it is based on the principle that many chemical agents are excreted through the skin in small quantities. The chemical agents may be:

(a) exogenous—e.g., drugs of abuse, environmental pollutants, prescription drugs, herbicides, pesticides etc.;

(b) endogenous—e.g., hormones, or metabolites such as glucose, creatinine or electrolytes.

The advantage of this device is that it provides quantitative information about the mean integrated exposure to chemical agents over long periods (e.g. several hours or days), and provides evidence of exposure even after the agent may have been completely metabolised or excreted from the body.

Frequently in the course of medical treatment, it is important for the physician to determine whether or not the patient is following the prescribed medical regimen, or is using alcohol or non-prescribed drugs. It is often the case that the patient does not disclose the relevant information accurately. Thus, there is a need for a monitoring device that could be used with convenience by the patient and which would yield accurate and precise information to the physician.

Prior to this invention, such a monitoring device was described in U.S. Pat. No. 4,329,999. The present invention constitutes a substantive improvement over the sweat patch device described in the above patent. In a comparison study using both the sweat patch and the transdermal dosimeter, the drug in question was not detected by the sweat patch, whereas good uptake was observed with the transdermal dosimeter. The superiority of the transdermal dosimeter is due largely to the creation of a dermal contact bridge: a fluid phase in the layer of the absorptive matrix that adjoins the skin surface. The dermal contact bridge provides an unbroken fluid link between tissue fluids in the skin and the collecting component of the transdermal dosimeter, allowing ultimately for a greater uptake of solutes excreted through the skin.

SUMMARY OF THE INVENTION

The present invention is a transdermal dosimeter for use in clinical studies which comprises:

A sealed adhesive container which is constructed of chemically inert, flexible, adhesive material impermeable to fluids and whose function it is to contain the other components of the dosimeter;

A dermal contact bridge which comprises two structural components, a fluid phase and solid support phase and whose function it is to act as an extension of the interstitial fluid of the skin and when necessary to act as a semi-permeable membrane separating the isotonic interstitial fluid from the hypertonic phase of the collecting component;

A collecting component which may comprise the same material as the solid phase of the dermal contact bridge or may be of a dry highly absorbent material with high fluid capacity and where either of the above may be impregnated with an osmotically active crystalloid material and whose function it is to provide storage for fluid and chemical substances collected by the dermal contact bridge, said collecting component being adjacent to and in contact with the dermal contact bridge; and A processing component which contains reagents which bind or react with the collected substances, said processing component being adjacent to and in contact with the collecting component.

BRIEF DESCRIPTION OF THE DRAWINGS

FIG. 6 graphically illustrates the results described in Example 1 ("A Clinical Trial of the Transdermal Dosimeter").

DETAILED DESCRIPTION OF THE INVENTION

The subject of this invention, a transdermal dosimeter is an adhesive device applied to the surface of the skin. It is watertight, and may be worn during the normal activities of daily life, including exercise and bathing. It has four separate functions:

(1) The facilitation of continuous transmission of substances from the surface of the skin into the device;

(2) Storage of liquid and chemical compounds;

(3) Binding of collected chemical compounds to inhibit back diffusion across the skin, or (4) Chemical conversion of collected substances to produce an observable color change in the device.

In practice, the device is affixed to the skin of a human subject and removed several hours or days later. The chemical agent under investigation may be extracted from the dosimeter (e.g., by centrifugation if in solution or chemical elution if bound) and then assayed by conventional laboratory techniques. Alternatively, the assay may be performed in situ in the transdermal dosimeter, using such methods as enzyme-linked colorimetric reactions or head space assay of volatile compounds. The concentration of chemical substances in the device provides both qualitative and quantitative information about the intensity of the subject's exposure to the substance under investigation.

Figure 1:
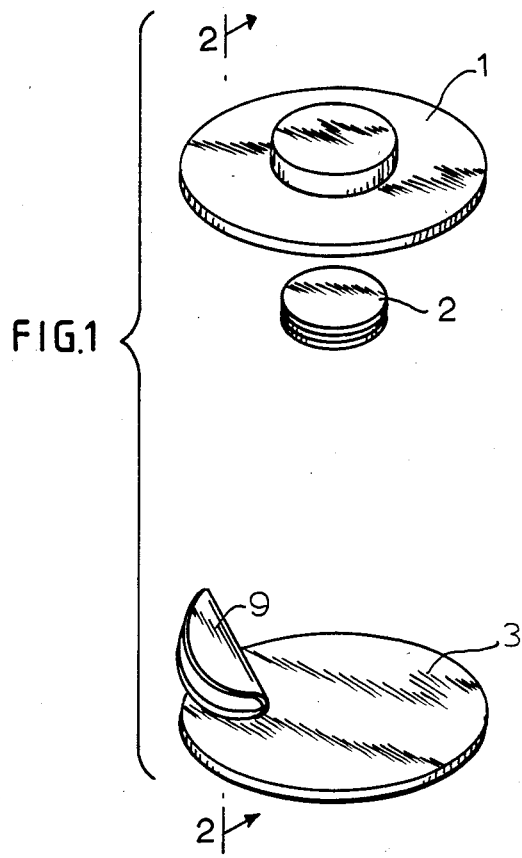
FIG. 1 shows the basic components of the transdermal dosimeter.
Figure 2:
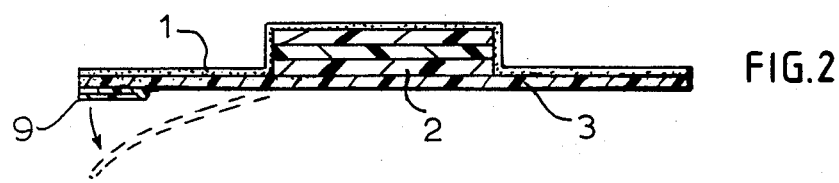
FIG. 2 is a cross section of the transdermal dosimeter.

FIGS. 1 and 2 show the transdermal dosimeter, both in terms of its basic components and as a cross-section in its assembled form.

The sealed adhesive container 1 is constructed or molded from flexible pressure sensitive adhesive tape(s). Its structure is not critical, provided it:

(1) holds the dermal contact bridge in intimate contact with the surface of the skin;

(2) contains the other components of the device;

(3) is watertight, chemically inert and non-allergenic;

(4) is aesthetically acceptable to the wearer.

The sealed adhesive container encloses three components: the dermal contact bridge, the collecting component and the processing component. These will be referred to for convenience as the functional pad 2 and will be described in more detail later. A backing member 3 seals the functional pad from the atmosphere.

Figure 3:
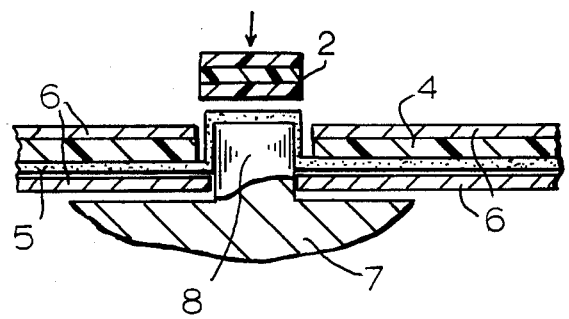
FIGS. 3-4 show the steps involved in making the transdermal dosimeter.

Referring to FIG. 3, the following steps are involved in the manufacture of the dosimeter.

A polystyrene sheet is cut into a square 5, 7 cm×7 cm in size. A hole 21 mm in diameter is cut out in the center of the square. A strip 6 of smooth-surfaced plastic type adhesive tape such as Hy-tape surgical tape, preferably 2 inches wide, is applied to the polystyrene square.

The above double-layered intermediate unit is sandwiched in a template as shown in FIG. 3. The device shown in FIG. 3 consists of two rigid plates 6 that clamp the double-layered intermediate unit, and a punch 7, which is used to form a pocket in the adhesive. The pocket is formed by blowing hot air onto the sticky surface of the adhesive tape, exposed through the hole in the assembly and force pressing the adhesive through the hole with the anvil 8 of the punch.

After the desired size pocket is formed, the double-layered unit shown in FIG. 3 is maintained with the punch in situ for at least 48 hours to prevent the adhesive tape from resuming its original shape. During this period, the heat treatment is discontinued.

Figure 4:
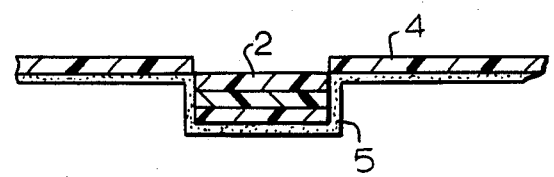

The double layered unit is removed from the assembly and the functional pad 2 is applied to the adhesive surface of the extruded pocket. The pocket is evaginated by applying pressure to the top of the functional pad. The final product of this operation is shown in FIG. 4.

A second portion of polystyrene material, ultimately to be a backing member 3 is cut into a square 7 cm×7 cm. This square is fixed to the adhesive surface of the container. A longitudinally folded strip of vinyl film 9, 2 cm. wide is placed at one edge of this double element between the polystyrene and the adhesive tape. The vinyl acts as the stripping element in the dosimeter, facilitating the removal of the backing member 3.

A disc, preferably 1⅝ inches (41.3 mm) in diameter is formed by stamping, out of the assembled element with the chamber containing the functional pad at the center of the disk. The transdermal dosimeter is now complete.

In a routine application, the backing member 3 is stripped off, thus exposing the adhesive surface of the sealed adhesive container 1. The unit can then be applied to the skin.

Figure 5:
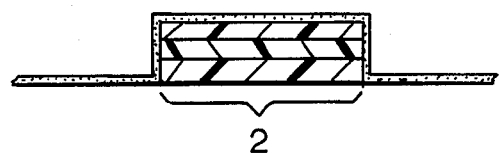
FIG. 5 shows a cross-section of the functional layers (functional pad) of the transdermal dosimeter.

FIG. 5 shows a cross-section of the functional pad 2 in the standard dosimeter. In this version the pad consists of three separate layers. The first layer is the dermal contact bridge (DCB). It is the layer that is in direct contact with the skin.

The dermal contact bridge serves two functions:

(1) It provides a functional extension of the interstitial fluid of the skin, so that fluids and chemical substances diffuse freely from the interstitial fluid into the DCB.

(2) If the collecting component contains a reservoir of hyperosmolar material, the DCB acts as a semipermeable membrane separating the isotonic interstitial fluid from the hypertonic phase.

The DCB has two structural components:
(a) a fluid phase, and
(b) a solid support phase.

The composition of the fluid phase is determined by the physico-chemical properties of the chemical compound under specific investigation. It may be:—aqueous e.g. normal or hypertonic saline (to facilitate collection of polar compounds or compounds with high water solubility)—lipid—e.g. mineral oil or vegetable oil (to facilitate collection of compounds with high lipid solubility)—organic—e.g. polyethylene glycol (PEG) (to facilitate collection of compounds with intermediate solubility).

The solid phase acts as a matrix to support the liquid phase. It may be cellulose based (e.g. filter paper), an inert polymer, a viscous organic compound (e.g. high molecular weight polyethylene glycol or a lipid ointment base), a semi-solid material such as a gel, or any other substance capable of holding immobilized fluid in close apposition to the surface of the skin.

The second or intermediate layer is the collecting component. The function of this component is to provide storage for fluid and chemical substances collected from the skin by the DCB. Its composition may be:

(1) The same as the solid phase of the DCB;

(2) A dry reservoir with high fluid capacity (e.g. cellulose based absorbent material or felted polyester);

(3) As a special application, either (1) or (2) impregnated with an osmotically active crystalloid material (e.g. sodium chloride, fructose, mannitol or urea) to generate an osmotic gradient across the DCB which acts as a semi-permeable membrane.

The third layer is the processing component. The function of this component is to chemically process the collected chemical substance(s) in some fashion so that they no longer remain free to diffuse back across the DCB into the skin. This serves to increase the sensitivity of the device. Processing occurs in either of two ways: binding or chemical conversion. When the processing component acts by binding, the substance becomes physically or chemically bound. The binding agent may be a non-specific chemical binding agent (e.g., activated charcoal) or a specific binding agent (e.g., an antibody to a specific compound or drug). When the transdermal dosimeter is removed from the skin, the chemical substance may be eluted from the binding agent, and assayed in the laboratory by conventional techniques. Alternatively, the processing component may act by chemical conversion of the substance under investigation, to yield a colored compound and/or a more readily stored product. Examples include:—enzymic conversion of ethanol to acetaldehyde with alcohol dehydrogenase, in which the coenzyme NAD is converted to NADH, and reconversion to NAD may be accomplished by a number of dyes which change color in the process,—chemical precipitation of chloride ions with silver nitrate to form dark-colored silver chloride. This is of potential use in screening for diseases such as cystic fibrosis, in which sweat chloride excretion is impaired.

The transdermal dosimeter may incorporate a number of chemical additives such as nystatin, sodium fluoride and reduced methylene blue.

The purpose of the additives is as follows:

Nystatin Inhibits fungal proliferation. Fungi normally resident on the surface of the skin might otherwise contaminate the sweat specimen, causing (a) metabolic breakdown of ethanol (to acetaldehyde and water); and/or (b) metabolic breakdown of glucose in sweat, generating ethanol and methanol de novo.

Sodium fluoride: Inhibits anaerobic glycolysis in bacteria and fungi normally resident on skin. It provides a safeguard against any of these organisms contaminating the sweat with products of anaerobic glycolysis, e.g., ethanol.

Reduced methylene blue: In a wet patch this turns bright blue in the presence of oxygen. Hence it is a visual indicator (when the patch is removed) that the patch has leaked and/or been tampered with.

The layers thus formed are then subjected to other necessary treatments. Thus, the dermal contact bridge must be wetted with the appropriate fluid as described above. Likewise the collecting and the processing components must be treated with appropriate materials.

The layers so formed constituting the functional unit are then placed inside the sealed adhesive container. It is noted that the transdermal dosimeter is waterproof.

Two modifications of the transdermal dosimeter have been successfully designed.

In modification A, a transdermal dosimeter is made exactly as described above, except that the dermal contact bridge and the collecting component are combined into a single layer i.e., the sealed adhesive container covers a two-layered component rather than a three-layered component.

This may be achieved in several ways, provided that this new combined layer fulfills the functions of the two original layers i.e. (a) providing a fluid bridge in intimate contact with the surface of the skin, and (b) providing a structure that will retain body fluids as well as their dissolved chemical substances.

Structural approaches include:

(i) solid absorptive matrix (e.g. paper, cellulose fiber, polyester fiber) pre-soaked in fluid. The matrix can be impregnated with crystalloid or other materials, to generate an osmotic gradient across the skin. The fluid phase may be aqueous, lipid, or organic.

(ii) semi-solid absorptive matrix (e.g. a gel) capable of absorbing fluids and dissolved substances, while simultaneously functioning as a dermal contact bridge in intimate contact with the surface of the skin.

In modification B, the transdermal dosimeter is made exactly as described above, except that all three components under the sealed adhesive container are combined into a single layer which combines their separate functions.

This may be achieved by modifying the combined dermal contact bridge and collecting component (described above in structural modification A) to also include the functions of the processing component.

There are two broad approaches to this modification:

(a) Incorporation of a binding material (e.g. activated charcoal, or a resin capable of binding organic substances, such as Tenax GC) into the combined layer described in modification A.

(b) Incorporation of the chemical conversion agents (described above) into the combined layer described in modification A.

The transdermal dosimeter offers many advantages. It is inexpensive to make and can be made from readily available materials. The device is convenient to apply and is well tolerated by wearers. It provides a simple, non-invasive method for monitoring exposure to chemical agents such as environmental toxins, prescription drugs, drugs of abuse and substances normally present in the blood which may be elevated in disease states (e.g., glucose in diabetics).

The subject matter of this invention is a considerable improvement over the prior art, i.e., the sweat patch of U.S. Pat. No. 4,329,999. In a clinical study comparing the sweat patch with the transdermal dosimeter, where a human subject was monitored for exposure to theophylline, none was detected after assaying the sweat patch, whereas the drug was readily detected by the transdermal dosimeter. This improvement is due to the presence of the fluid phase in the dermal contact bridge. In a study where pads were damp (loaded with 50 $\mu$l of fluid) uptake of theophylline was lower as compared to assays where pads were wet (loaded with 100 $\mu$l of fluid).

The incorporation of activated charcoal into the processing component is a further improvement over the prior art. The activated charcoal impregnated Whatman filter paper bound 23.45% more of theophylline than untreated Whatman filter paper.

The following examples describe the manner and process of making and using the invention and represent the best mode contemplated by the inventor, but are not to be construed as limiting.

EXAMPLE 1

A Clinical Trial of the Transdernal Dosimeter

A clinical study was performed to compare the function of the transdermal dosimeter with the standard sweat-patch test.

A healthy 41 year old male ingested a sustained-release theophylline preparation (Theo-Dur, Key Pharmaceuticals) in a low dose—200 mg twice daily, for four days. At the same time as the drug was commenced, the monitoring devices were affixed to the skin of the forearms and ankles on day zero and removed after they had been worn for approximately 72 hours. Single layer (modification B) transdermal dosimeters (TDD) were used. They comprised a solid absorptive matrix (disks of heavy grade Whatman filter paper, ⅜ inch diameter) pre-soaked in fluid (quantity and nature specified below). No binding material or chemical conversion agent was included. The sealed adhesive container was molded from a disk of adhesive Hytape (1.5 inches diameter). The following devices were affixed in duplicate pairs:

Standard sweat-collecting patch (3M model)
TDD (loaded with 50 microliters normal saline)
TDD (loaded with 100 microliters normal saline)
TDD (loaded with 100 microliters saturated sodium chloride solution)

Extraction of fluid sample: The above devices were removed from the skin after being worn for approximately 72 hours, and the fluid phase extracted by centrifugation. The theophylline content of the fluid phase was assayed by Fluorescence Polarization Immunoassay (Abbott). The theophylline content (in micrograms per milliter) of the fluid phase from each collecting device is shown in the following table (A and B represent duplicate collections):

| Device | Load | A | B |
|---|---|---|---|
| Sweat patch (3M) | none | N.D. | N.D. |
| TDD + normal saline | 50 $\mu$l | 0.32 | 0.40 |
| TDD + normal saline | 100 $\mu$l | 0.64 | 0.49 |
| TDD + saturated NaCl solution | 100 $\mu$l | 0.66 | 0.63 |

(N.D. = None detected, i.e., concentration below lower limit of sensitivity of assay)

(These results are shown graphically in FIG. 6). When the devices were centrifuged, the TDD's with saturated sodium chloride solution contained a larger volume of fluid than any of the other collecting devices.

It was concluded that:

(1) There was no detectable theophylline in the fluid collected in the standard 3M sweat-collecting patches.

(2) Theophylline concentrations were lower in the TDD's loaded with 50 µl fluid compared with those loaded with 100 µl fluid, possibly because the pads were damp rather than wet, precluding efficient function as a dermal contact bridge (DCB).

(3) There was good agreement between 3 out of the 4 TDD's loaded with 100 µl fluid, and close agreement between both TDD's loaded with 100 µl saturated sodium chloride. This suggests that optimal conditions operate when (a) there is an efficient fluid bridge between the DCB and the skin, and (b) there is an osmotic gradient between the interstitial fluids of the body and the collecting system of the TDD.

EXAMPLE 2

Effect of a Binding Component in the Transdermal Dosimeter

A study was performed to measure in-vitro binding of theophylline by the activated charcoal in the transdermal dosimeter.

A theophylline standard solution (40 µg/ml) was prepared from a commercial assay standard (Abott Laboratories, North Chicago, Ill.). Four disks of heavy grade Whatman filter paper ($\frac{7}{8}$ inch diameter) were prepared. Two of these were stapled to disks ($\frac{5}{8}$ inch diameter) of Teflon coated with activated charcoal (AC) (3M Corp) The resulting four disks (two of filter paper (FP) and two of filter paper stapled to Teflon/AC (FP/AC) were each placed in a test tube, and loaded with 200 µl of the standard theophylline solution. Each test tube was sealed with a rubber stopper and incubated at room temperature (21° C.) for 30 minutes. At the end of this time, the disks were removed from the test tubes. The fluid phase was extracted and assayed for theophylline content as described above (under Extraction of Fluid sample in Example 1: "Clinical trial of the transdermal dosimeter"). The theophylline content (in micrograms per milliliter) of the fluid phase from each disk is shown in the following table (A and B represent duplicate collections):

| Source | A | A | Mean |
|---|---|---|---|
| Standard theophylline solution | 38.9 | | |
| Filter paper alone | 34.8 | 34.7 | 34.75 |
| Filter paper + activated charcoal | 22.6 | 30.6 | 26.6 |

It was concluded that:

(1) The mean of the theophylline concentrations showed a reduction from 34.75 (filter paper alone) to 26.6 (filter paper+AC) i.e. the concentration was reduced by a mean value of 23.45%. This demonstrates that theophylline is bound significantly by activated charcoal in an in-vitro simulation of the transdermal dosimeter.

(2) The variation between the two sets of results from the filter paper/AC combinations probably arises from the relatively crude fashion in which the aqueous phase was held in apposition with the AC; stapling of the two layers probably resulted in unequal surface area contact in the two specimens (3) These results demonstrate in principle that drugs (such as theophylline) may be bound by binding agents (such as activated charcoal) in the transdermal dosimeter. Since substances bound to AC may be readily eluted (with agents such as carbon disulfide) for subsequent assay, these findings demonstrate that the sensitivity of the transdermal dosimeter may be enhanced by the incorporation of binding agents.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

What is claimed:

1. A transdermal dosimeter for use in a diagnostic test which comprises:
   (a) a sealed container constructed of chemically intert, flexible, fluid-tight, adhesive material;
   (b) a dermal contact bridge in the container which comprises a fluid component and a support means component for supporting the fluid component within the container;
   (c) a collecting component means in the container and in contact with the dermal contact bridge, for providing storage for fluid substances collected from the dermal contact bridge, said collecting component means being impregnated with an osmotically active crystalloid material; and
   (d) a process component in the container made of fluid absorbent material containing a chemical reagent which reacts with the stored substances, said process component being in contact with the collecting component.

2. The apparatus of claim 1 wherein the fluid is aqueous.

3. The apparatus of claim 2 wherein the fluid contains an osmotically active solute.

4. The apparatus of claim 2 wherein the fluid is saline.

5. The apparatus of claim 2 wherein the fluid is saturated with NaCl.

6. The apparatus of claim 5 wherein the fluid is mineral oil.

7. The apparatus of claim 5 wherein the fluid is vegetable oil.

8. The apparatus of claim 7 wherein the fluid is polyethylene glycol.

9. The apparatus of claim 1 wherein the fluid is lipid.

10. The apparatus of claim 1 wherein the fluid is organic.

11. The apparatus of claim 1 wherein the support means is of cellulose-type material.

12. The apparatus of claim 11 wherein the support means is a high molecular weight polyethylene glycol.

13. The apparatus of claim 11 wherein the support means is a gel.

14. The apparatus of claim 1 wherein the support means is an inert polymer.

15. The apparatus of claim 1 wherein the support means is a viscous organic compound.

16. The apparatus of claim 1 wherein the processing component contains a non-specific binding agent.

17. The apparatus of claim 1 wherein the processing component contains activated charcoal.

18. The apparatus of claim 1 wherein the processing component contains a specific binding agent.

19. The apparatus of claim 1 wherein the processing component contains an antibody.

20. The apparatus of claim 1 wherein the chemical reagent include an enzyme and chemical agents to form colored compounds from the products of the enzymically catalyzed reactions.

21. The apparatus of claim 1 wherein the chemical reagent include chemical compounds which can react with substances present in human tissue fluids to yield a colored product.

22. The appratus of claim 1 wherein the processing component contains silver nitrate.

23. The apparatus of claim 1 wherein the dermal contact bridge and the collecting component are combined into a single layer.

24. The apparatus of claim 23 wherein the single layer comprises a solid absorptive matrix pre-soaked in fluid.

25. The apparatus of claim 23 wherein the single layer comprises a semi-solid absorptive matrix.

26. The apparatus of claim 1 wherein the dermal contact bridge, the collecting component, and the processing component are combined into a single layer.

27. The apparatus of claim 26 wherein a binding agent is incorporated.

28. The apparatus of claim 27 wherein the binding material is activated charcoal.

29. The apparatus of claim 27 wherein the binding material is a resin.

30. The apparatus of claim 26 wherein a chemical conversion agent is incorporated.

31. A diagnostic test, which comprises the steps of:
providing a dosimeter which comprises;
 (a) a sealed container constructed of chemically inert, flexible, fluid-tight, adhesive material;
 (b) a dermal contact bridge which comprises a fluid component and a support means component for supporting the fluid component within the container;
 (c) a collecting component means in the container and in contact with the dermal contact bridge, for providing storage for fluid substances collected from the dermal contact bridge, said collecting component means being impregnated with an osmotically active crystalloid material; and
 (d) a process component in the container made of fluid absorbent material containing a chemical reagent which reacts with the stored substances, said process component being in contact with the collecting component;
affixing the dosimeter to the skin of a test subject;
removing the dosimeter after a period of time; and
determining the results of the test.

* * * * *

UNITED STATES PATENT AND TRADEMARK OFFICE
CERTIFICATE OF CORRECTION

PATENT NO. : 4,595,011
DATED : June 17, 1986
INVENTOR(S) : Michael Phillips

It is certified that error appears in the above-identified patent and that said Letters Patent is hereby corrected as shown below:

Column 6, line 17, "Transdernal" should be --Transdermal--.

Column 6, line 32, "1/3" shouldbe --7/8--.

Signed and Sealed this

Twenty-third Day of September 1986

[SEAL]

Attest:

DONALD J. QUIGG

Attesting Officer

Commissioner of Patents and Trademarks